(12) United States Patent
Bettenga et al.

(10) Patent No.: US 10,945,853 B2
(45) Date of Patent: Mar. 16, 2021

(54) GLENOID IMPLANT AND METHOD OF USE THEREOF

(71) Applicant: Smith & Nephew, Inc., Memphis, TN (US)

(72) Inventors: Mason Bettenga, Memphis, TN (US); Jeff Wyman, Memphis, TN (US); Dirk Wunderle, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 56 days.

(21) Appl. No.: 16/327,923

(22) PCT Filed: Sep. 13, 2017

(86) PCT No.: PCT/US2017/051311
§ 371 (c)(1),
(2) Date: Feb. 25, 2019

(87) PCT Pub. No.: WO2018/052965
PCT Pub. Date: Mar. 22, 2018

(65) Prior Publication Data
US 2019/0201206 A1    Jul. 4, 2019

Related U.S. Application Data

(60) Provisional application No. 62/396,389, filed on Sep. 19, 2016.

(51) Int. Cl.
*A61F 2/40*    (2006.01)
*A61F 2/30*    (2006.01)
*A61B 17/04*   (2006.01)
*A61F 2/46*    (2006.01)

(52) U.S. Cl.
CPC ........ *A61F 2/4081* (2013.01); *A61B 17/0401* (2013.01); *A61F 2/30734* (2013.01); *A61F 2/30749* (2013.01); *A61F 2/30771* (2013.01); *A61F 2/4612* (2013.01); *A61B 2017/0404* (2013.01); *A61F 2002/30011* (2013.01); *A61F 2002/30062* (2013.01); *A61F 2002/3092* (2013.01); *A61F 2002/3093* (2013.01); *A61F 2002/30153* (2013.01); *A61F 2002/30224* (2013.01); *A61F 2002/30561* (2013.01); *A61F 2002/30601* (2013.01); *A61F 2002/30733* (2013.01); *A61F 2002/30878* (2013.01); *A61F 2002/30985* (2013.01); *A61F 2310/00023* (2013.01); *A61F 2310/00131* (2013.01);
(Continued)

(58) Field of Classification Search
CPC combination set(s) only.
See application file for complete search history.

(56) References Cited

U.S. PATENT DOCUMENTS

2013/0238099 A1*  9/2013  Hardy .................. A61F 2/4081
                                              623/19.11
2013/0261752 A1* 10/2013  Lappin ................. A61F 2/4081
                                              623/19.11

* cited by examiner

*Primary Examiner* — Yashita Sharma
(74) *Attorney, Agent, or Firm* — Burns & Levinson, LLP; Joseph M. Maraia; Marlo Schepper Grolnic (57) ABSTRACT

A glenoid implant that is 3D-printed or machined from ceramic and/or metal as a substitute for an autograft or allograft in a surgical repair. Structural supports composed of metal are designed in the interior of the implant for support during implantation and post-operation. The remainder of the volume of the implant is composed of a material having optimal pore structure for rapid bone integration and healing.

13 Claims, 6 Drawing Sheets

(52) U.S. Cl.
CPC ............... *A61F 2310/00179* (2013.01); *A61F 2310/00293* (2013.01)

GLENOID IMPLANT AND METHOD OF USE THEREOF

CROSS-REFERENCE TO RELATED APPLICATIONS

This application is the U.S. national phase entry under 35 U.S.C. § 371 of International Application No. PCT/US2017/051311, filed Sep. 13, 2017, entitled GLENOID IMPLANT AND METHOD OF USE THEREOF, which in turn claims priority to and benefit of U.S. Provisional Application No. 62/396,389, filed Sep. 19, 2016, the contents of which are incorporated herein by reference in their entirety for all purposes.

FIELD

The present disclosure relates to surgical implants and, more particularly, to implants for an anatomical feature such as a glenoid.

BACKGROUND

The shoulder joint, also referred to as the glenohumeral joint, is the joint between the glenoid cavity (a part of the scapula) and the head of the humerus or upper arm bone. The glenoid cavity is shallow, covering only about a third of the head humeral head. As a result, the glenoid cavity provides relatively little bony constraint upon motion of the humerus and the glenohumeral joint exhibits the widest range of motion of all joints in the human body. While the glenohumeral joint is also constrained by soft tissue (e.g., cartilage attached to the rim of the glenoid cavity, tendons, etc.), soft tissue in general cannot provide the same degree of constraint as bone. Accordingly, it is relatively easy to force the humerus from its normal anatomical position with respect to the glenoid socket, that is, to dislocate the shoulder. While not life threatening, a dislocated shoulder can cause pain and immobilization of the joint, impacting a patient's lifestyle.

In the case of severe bone loss caused by shoulder instability and/or dislocation, the current standard of care is to attach a small tissue graft from a donor (allograft) or directly from the patient (autograft) to the lesion to restore the bony anatomy. However, autograft taken from the patient, generally from the iliac crest, is time-consuming during the repair procedure and painful for the patient. Allograft is more efficient, but not optimal, since it comes from a foreign source. Moreover, both autograft and allograft require manual harvesting and shaping during the repair procedure. Not only do these procedures consume a significant amount of time that the patient is under anesthesia, but they also lead to higher costs due to additional operating room time.

SUMMARY

Described herein is a glenoid implant that is additive-manufactured (i.e., 3D-printed) or machined from ceramic and/or metal as a substitute for autograft or allograft. The implant can be made in one step and is sized to be passed through a cylindrical arthroscopic cannula.

Structural supports composed of a biocompatible metal (e.g. titanium or tantalum) can be designed in the interior of the implant for support during implantation and post-operation.

The remainder of the volume of the implant is composed of a material having optimal pore structure for rapid bone integration and healing (e.g. sintered hydroxyapatite or tricalcium phosphate). The side of the implant which faces the glenoid can be optimized for surface roughness, porosity and macrotextural features to improve initial fixation.

The implant may also include telescoping cylinders or pegs sintered into the structural support portion of the implant in the retracted position with minimal contact to the implant.

Metal or all-suture buttons could be deployed through the pegs into the glenoid. Once compression is applied by the user, the attachment points of the pegs break away by design and the pegs deploy into mating holes of the glenoid, providing extra shear stability to the implant during healing.

Further examples of the glenoid implant of this disclosure may include one or more of the following, in any suitable combination.

In examples, the glenoid implant of this disclosure includes a substantially rectangular body having a solid structural support and a porous region surrounding the structural support. The body has a first surface, a second surface opposite the first surface, and at least two through holes extending through the structural support from the first surface to the second surface. At least one cylinder is disposed within each of the at least two through holes, each cylinder having a telescoping peg configured to extend from the second surface into a mating hole in the glenoid.

In further examples, the structural support is made of a biocompatible metal, which may be one of titanium or tantalum. The porous region is made of a resorbable ceramic and/or a semi-crystalline bioinductive/bioconductive material. The porous region may be made of one of hydroxyapatite (HA) or tricalcium phosphate (TCP), and at least one surface of the implant may be coated with HA or TCP. The second surface of the body has features for improving fixation strength of the body against the glenoid. In examples, the implant is additive manufactured.

Examples of the method of glenoid instability repair of this disclosure includes: 1) forming at least two axially-aligned passages from an anterior surface to a posterior surface of a glenoid; 2) aligning at least two through holes of the implant described above with the at least two passages in the glenoid; and 3) applying a force to break a connection point between the peg and the implant body, causing the peg to extend from the second surface of the body into one of the at least two passages of the glenoid.

In further examples, the method further includes passing a fixation device attached to a suture through at least one of the at least two through holes, such that the fixation device abuts the at least one cylinder and the suture extends from the posterior surface of the at least one passage. Applying the force to break the connection point between the peg and the implant body may be caused by pulling the suture in a direction substantially opposite the fixation device. The method may further include passing the implant through an arthroscopic cannula to a repair site including the glenoid. Advantageously, use of the glenoid implant of this disclosure allows quicker wound closure time and thus less time under anesthesia for the patient. It also leads to a faster recovery time.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Figure 1A:
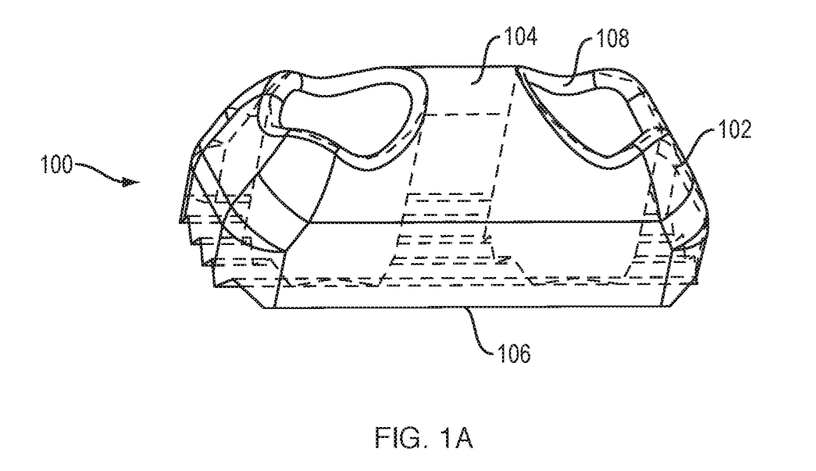
FIGS. 1A and 1B show an exemplary glenoid implant of this disclosure in a front perspective view (FIG. 1A) and a top perspective view (FIG. 1B)

Referring now to FIG. 1A, an exemplary glenoid implant 100 of this disclosure is shown in a transparent, front perspective view. The implant 100 includes a substantially rectangular body 102 having a first surface 104 and a second surface 106 opposite the first surface 104. The body 102 is sized to pass through a cylindrical arthroscopic cannula, as further described below. For example, the body 102 may have a width of about 8 mm, a height of about 8 mm and a length of about 20 mm, although other dimensions are contemplated by this disclosure, depending on the size of the cannula to be used. The implant 100 is preferably made by additive-manufacturing (i.e., 3D printed) as a substitute for an autograft or allograft, but could also be machined from ceramic and/or metal. The implant 100 may be mass-produced in one or more standard sizes. However, the implant 100 could also be customized to match a specific patient's glenoid features.

Figure 1B:
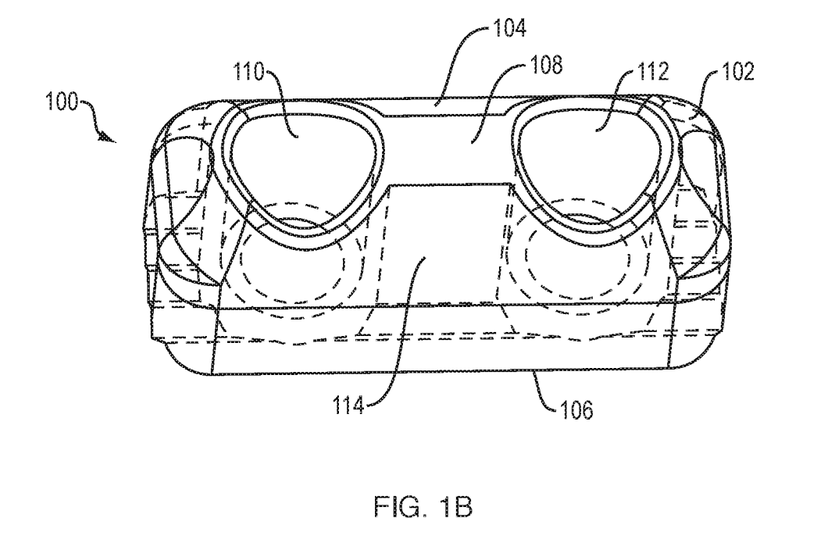

As shown in FIG. 1B, the body 102 includes a solid structural support 108 composed of implant-grade metals (e.g. titanium or tantalum), extending from the first surface 104 to the second surface 106. The structural support 108 may be in the form of at least two reinforced through holes (shown here for exemplary purposes as two through holes 110, 112) extending from the first surface 104 to the second surface 106, with a solid wall 114 extending therebetween.

In examples, a diameter of the through holes 110, 112 may be about 3 mm. The remaining portion of the body 102 surrounding the structural support 108 comprises a resorbable ceramic (e.g. sintered hydroxyapatite (HA) or tricalcium phosphate (TCP)). Preferably, the material surrounding the structural support 108 is a semi-crystalline bioinductive/bioconductive material that is optimized for porosity and strength. In examples, the body 102 could also be coated at the first surface 104 and/or the second surface 106 with HA and/or TCP to improve bony integration.

Figure 2:
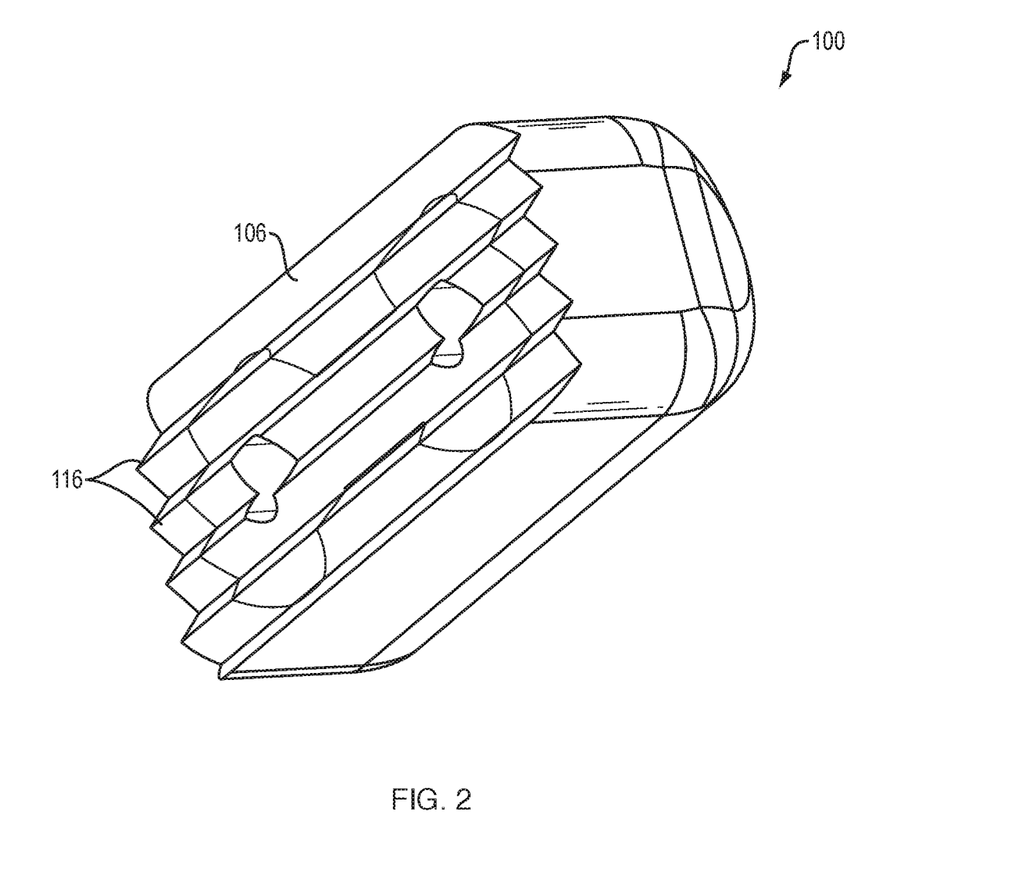
FIG. 2 illustrates a bottom surface of the implant of FIGS. 1A and 1B.

FIG. 2 illustrates the second (i.e., glenoid-facing) surface 106 of the implant 100 in more detail. As shown in FIG. 2, the second surface 106 comprises features 116 tailored to improve the initial fixation strength of the implant 100 against the bone. Examples of such features 116 may include surface roughness, porosity and/or macrotextural features.

Figure 3A:
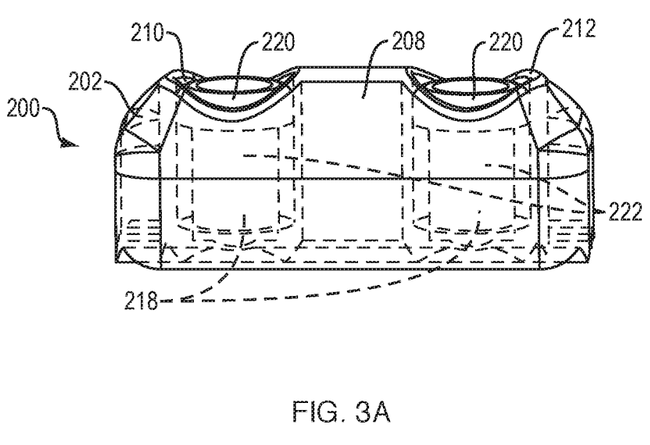
FIGS. 3A and 3B show another example of a glenoid implant of this disclosure having telescoping projections.

Another example of a glenoid implant 200 is shown in FIG. 3A. The implant 200 of FIG. 3A is essentially the same as the implant 100 of FIGS. 1A and 1B except that each of the two through holes 210, 212 have a hollow cylinder 218 disposed within. The cylinders 218 are comprised as the same material as the structural support 208, e.g., titanium or tantalum. Each cylinder 218 has a head portion 220 and a telescoping peg 222 attached to the head portion 220.

Figure 3B:
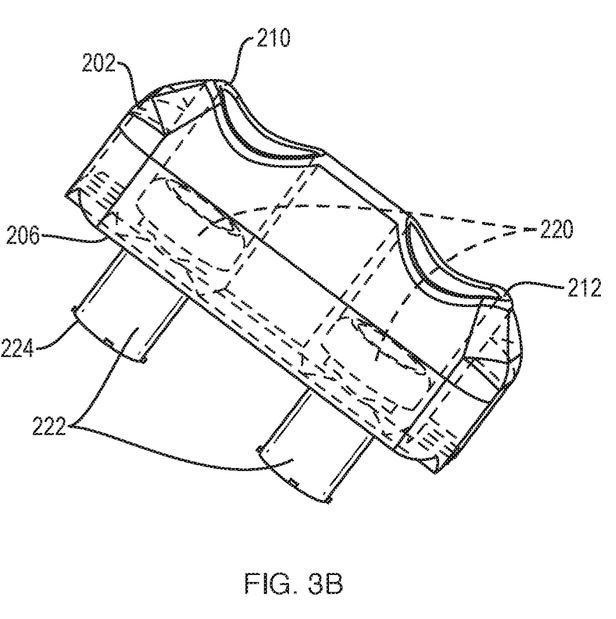

As shown in FIG. 3B, the peg 222 is configured to extend from the second surface 206 of the body 202 into a mating passage in bone (not shown) when the head portion 220 is disposed at the bottom of the through hole 210, 212. A connection point 224 is formed between the body 202 and the peg 222 during manufacturing and is designed to break when the user applies a small force to deploy the peg 222, as further described below. For example, the connection point 224 may include a reduced cross-sectional area between the body 202 and the peg 222. The reduced cross-sectional area is adapted to separate the body 202 and the peg 222 upon application of enough axial force and/or torque to break the connection point 224.

The discussion will now turn to FIGS. 4A-E, which illustrate of method of use of the implant 200 of FIGS. 3A and 3B. The implant 200 is shown as used in a shoulder instability repair. However, it is contemplated by this disclosure that the implant 200 could be adapted for use in other types of surgical repair.

Figure 4A:
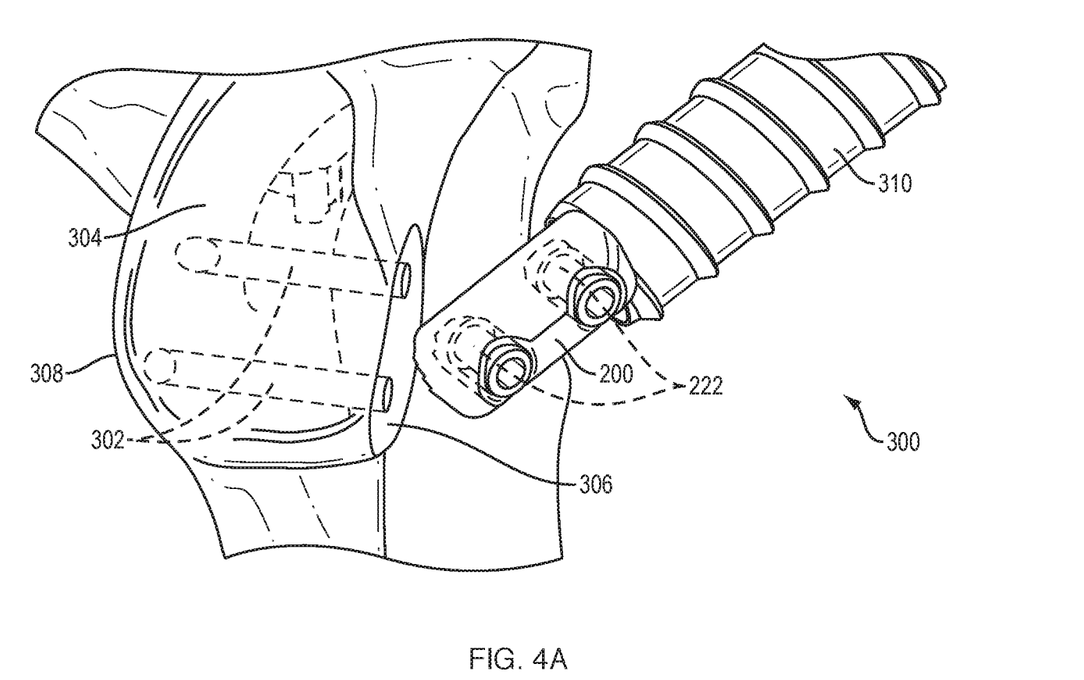
FIGS. 4A-E illustrate a method of using of the implant of FIGS. 3A and 3B in a shoulder instability repair.

FIG. 4A shows a portion of a patient's shoulder 300 in which axially aligned passages 302, which may be two passages placed about 10 mm apart, are initially drilled through the patient's glenoid 304. The passages are formed from an anterior surface 306 to a posterior surface 308 (or vice versa) by standard means known in the art. After the passages 302 are formed, the patient's shoulder 300 is prepared for insertion of the implant 200. Non-limiting examples of methods for preparing a patient's shoulder are described in U.S. Patent Publication No. 2014-0277185 (Boileau et al.), incorporated herein by reference. As discussed above, the implant 200, when the pegs 222 are in an undeployed position, is sized to pass through an arthroscopic cannula 310 extending from a surface of the patient's skin to the repair site including the patient's glenoid 302.

Figure 4B:
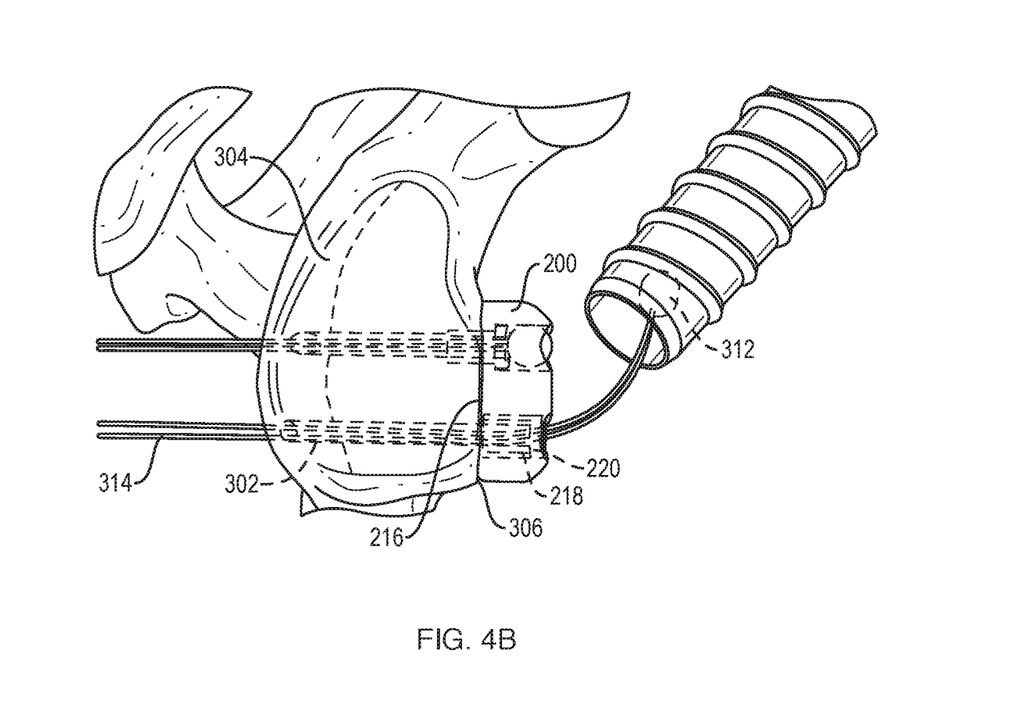

Next, as shown in FIG. 4B, a fixation device 312, which may be in the form of metal or all-suture button, and which has been previously attached to a suture 314, is passed through the cylinder 218 such that the suture 314 exits the passage 302, and the fixation device 312 rests on the head portion 220 of the cylinder 218. Non-limiting examples of metal buttons are described in U.S. Patent Publication No. 2012/0310279 (Sikora et al.), U.S. Patent Publication No. 2014-0277185 (Boileau et al.), and in the Endobutton family of products (manufactured by Smith & Nephew, Inc., Andover, Mass., USA), incorporated herein by reference. Non-limiting examples of all-suture buttons include the Q-Fix all-suture implant (manufactured by ArthroCare Corporation, Tex., USA) and generally described in U.S. Publication No. 2013/0123810 (Brown et al.), incorporated herein by reference. So positioned, the surface features 216 of the implant 200 engage the prepared anterior surface 306 of the glenoid 304 to increase the fixation strength of the implant 200 against the glenoid 304.

Figure 4C:
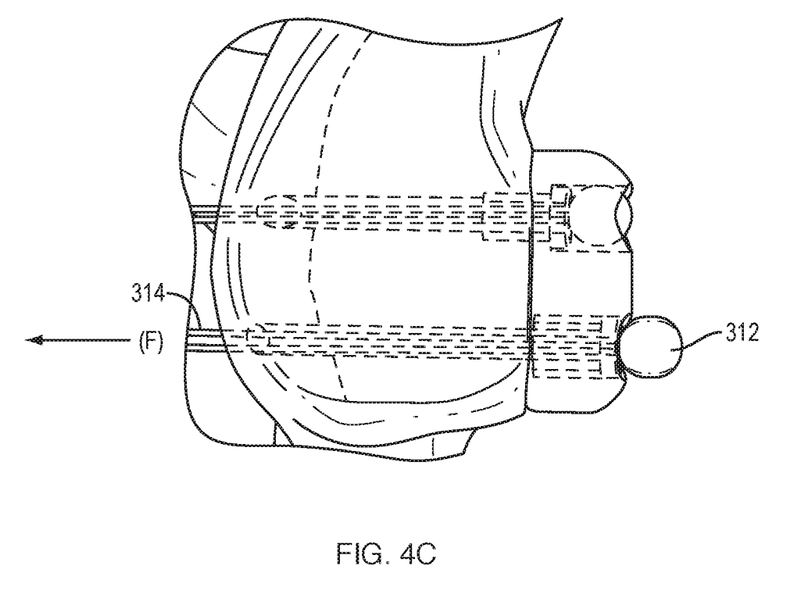
Figure 4D:
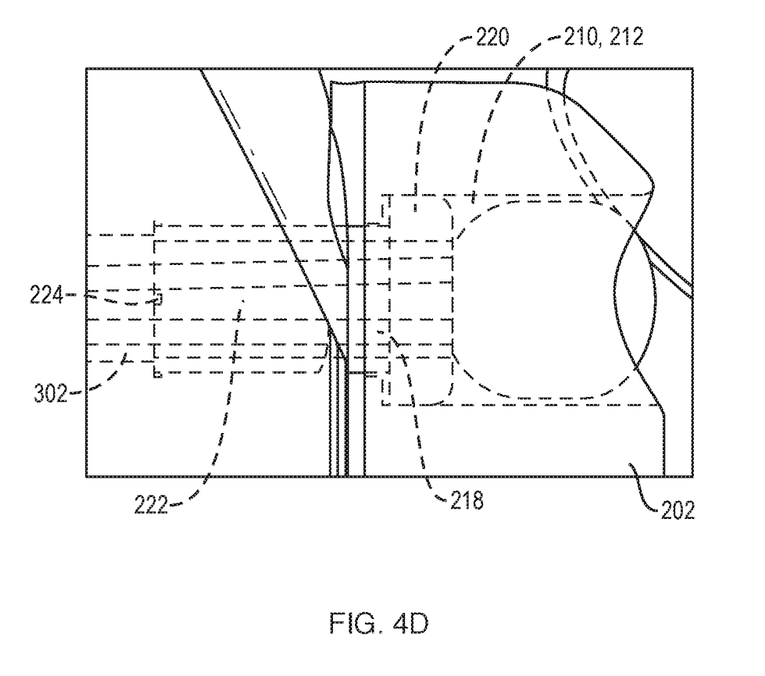
Figure 4E:
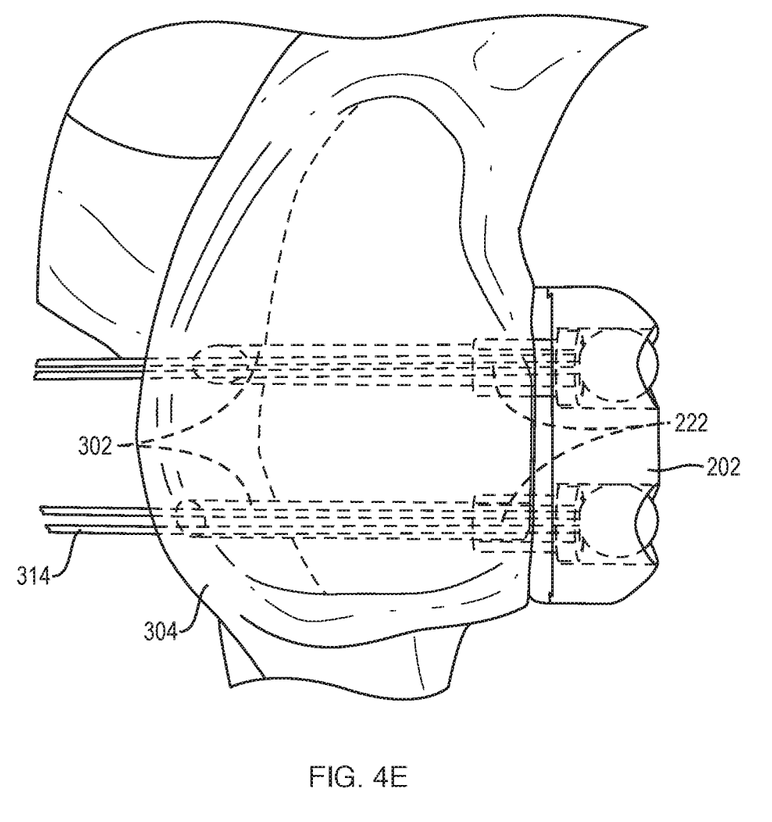

Turning now to FIG. 4C, the user then applies a slight pulling force (F) to the suture 314 in a direction substantially opposite the fixation device 312. As shown in FIG. 4D, the pulling force (F) causes the connection point 224 between the implant body 202 and the peg 222 to break. This in turn causes the head portion 220 of the cylinder 218 to descend to the bottom of the through hole 210, 212 and the peg 222 to be deployed into the passage 302. As shown in FIG. 4E, once the pegs 222 have been fully deployed into the passages 302, the pegs 222 provide additional shear stability across the fracture site for improved fixation strength of the implant body 202 against the glenoid 304. Surgical knots (not shown) may be then tied in the suture 314, fixing the implant body 202 into place. The ends of the suture 314 may then be trimmed.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. A surgical implant comprising:
   a substantially rectangular body having a solid structural support and a porous region surrounding the structural support, the body further having a first surface, a second surface opposite the first surface, and at least two through holes extending through the structural support from the first surface to the second surface;
   a cylinder disposed within each of the at least two through holes, the cylinder comprising a telescoping peg configured to allow passage of a suture through the cylinder; and
   a breakable connection point between the body and the cylinder, the connection point configured to secure the telescoping peg within the through hole until a force applied to the connection point allows the telescoping peg to extend from the second surface into a mating hole in bone.

2. The implant of claim 1, wherein the structural support comprises a biocompatible metal.

3. The implant of claim 1, wherein the structural support comprises one of titanium or tantalum.

4. The implant of claim 1, wherein the porous region comprises a resorbable ceramic.

5. The implant of claim 1, wherein the porous region comprises a semi-crystalline bioinductive/bioconductive material.

6. The implant of claim 1, wherein the porous region comprises one of hydroxyapatite (HA) or tricalcium phosphate (TCP).

7. The implant of claim 1, wherein at least one surface of the implant is coated with HA or TCP.

8. The implant of claim 1, wherein the second surface of the body comprises features for improving fixation strength of the body against the bone.

9. The implant of claim 1, wherein the implant is additive manufactured.

10. A method of glenoid instability repair comprising:
    forming at least two axially-aligned passages from a first surface to a second surface of a glenoid;
    aligning at least two through holes of an implant with the at least two passages in the glenoid, the implant further comprising:
       a substantially rectangular body having a solid structural support and a porous region surrounding the structural support, the body further having a first surface, a second surface opposite the first surface, the at least two through holes extending through the structural support from the first surface to the second surface, and a cylinder disposed within each of the at least two through holes, the cylinder comprising a telescoping peg configured to allow passage of a suture through the cylinder;
    applying a force to break a connection point between the peg and the implant body, causing the peg to extend from the second surface of the body into one of the at least two passages of the glenoid.

11. The method of claim 10, further comprising passing a suture attached to a fixation device through at least one of the at least two through holes, such that the fixation device abuts the at least one cylinder and the suture extends through the cylinder and from the at least one passage in the glenoid.

12. The method of claim 11, wherein applying the force to break the connection point between the peg and the implant body comprises pulling the suture in a direction substantially opposite the fixation device.

13. The method of claim 10, further comprising passing the implant through an arthroscopic cannula to a repair site including the glenoid.

* * * * *